(12) United States Patent
Specht et al.

(10) Patent No.: US 8,597,872 B2
(45) Date of Patent: Dec. 3, 2013

(54) METHOD FOR PRODUCTION OF A MEDICAL MARKER

(75) Inventors: Heiko Specht, Hanau (DE); Frank Krüger, Nidderau (DE)

(73) Assignee: Heraeus Precious Metals GmbH & Co. KG, Hanau (DE)

( * ) Notice: Subject to any disclaimer, the term of this patent is extended or adjusted under 35 U.S.C. 154(b) by 711 days.

(21) Appl. No.: 12/641,814

(22) Filed: Dec. 18, 2009

(65) Prior Publication Data

US 2010/0159396 A1 Jun. 24, 2010

(30) Foreign Application Priority Data

Dec. 19, 2008 (DE) .......................... 10 2008 063 676
Oct. 13, 2009 (DE) .......................... 10 2009 049 287

(51) Int. Cl.
*G03F 7/20* (2006.01)
(52) U.S. Cl.
USPC .......................... 430/321; 430/320; 430/324
(58) Field of Classification Search
None
See application file for complete search history.

(56) References Cited

U.S. PATENT DOCUMENTS

| | | | | |
|---|---|---|---|---|
| 3,811,973 A | * | 5/1974 | Lesh et al. | 216/18 |
| 5,454,928 A | * | 10/1995 | Rogers et al. | 205/125 |
| 6,203,732 B1 | * | 3/2001 | Clubb et al. | 264/81 |
| 6,635,082 B1 | * | 10/2003 | Hossainy et al. | 623/1.15 |
| 7,411,204 B2 | * | 8/2008 | Appleby et al. | 250/505.1 |
| 2005/0096729 A1 | * | 5/2005 | Donadio, III | 623/1.15 |
| 2006/0108678 A1 | * | 5/2006 | Kumar et al. | 257/690 |
| 2007/0162108 A1 | * | 7/2007 | Carlson et al. | 623/1.34 |
| 2008/0243069 A1 | * | 10/2008 | Krivoruchko | 604/103.1 |

FOREIGN PATENT DOCUMENTS

EP 1813367 A2 8/2007
WO 2007140635 A1 12/2007

* cited by examiner

*Primary Examiner* — Martin Angebranndt
(74) *Attorney, Agent, or Firm* — Panitch Schwarze Belisario & Nadel LLP (57) ABSTRACT

A method is provided for production of a medical marker (4) made of an X-ray-opaque material, including the following steps:
  a) photolithographic application of a mask (31) on a substrate (1);
  b) deposition of the X-ray-opaque material (40) of the marker (4) on the substrate (1);
  c) removal of the mask (31); and
  d) elimination of the substrate (1).

6 Claims, 8 Drawing Sheets

METHOD FOR PRODUCTION OF A MEDICAL MARKER

BACKGROUND OF THE INVENTION

The present invention relates to annular or tubular markers for catheters and to preferred production methods.

Markers are used for easier location of catheters in human or animal bodies and for this reason are generally opaque to X-rays. In this way, catheters or vessel supporting devices (stents), which are becoming smaller and smaller, can be more easily located. Typical markers have an outer diameter of approximately 100 to 600 µm, an inner diameter of approximately 40 to 500 µm, and a length of 0.5 to 2 mm.

From International application publication WO 2007/140635 A1, the use of markers for determining the position of catheters is known. In the distal end region of the catheters sit one or more radio-opaque, in, particular X-ray-opaque, sleeve-like markers on the wire shaft, which have essentially two functions. First, when the catheter is being used, the position of the guide wire tip should be easily recognizable in an X-ray imaging device—for example by an elongated marker coil directly on the distal end of the guide wire. Second, with the help of several markers arranged, for example, equidistant in front of the distal end, a length measurement of a stenosis to be treated could be performed on the X-ray imaging device. For this purpose, the markers must have an X-ray-opaque material, in order to achieve outstanding X-ray visibility. With known catheter guidance wires, there is the problem that, on the one hand, the wire should be as flexible as possible particularly on its distal end, in order to guarantee the most atraumatic insertion of the wire as possible into heart vessels and thereby an easy passage through narrow points and bends in the vessel course to be traversed.

Preferably, markers are placed on the catheters as rings or tubules. Such rings or tubules are cut from a long tube. Consequently, however, the dimensions are also limited. In order to achieve markers with smaller dimensions, small bands are placed around the catheters, whose mounting is, however, complicated as a result.

From the state of the art it is known to produce such markers either by drawing or cutting lengths of tubes or fusing foils. Fusing foils has proven to be disadvantageous, in particular because the fused connection is produced only unreliably. Cutting lengths of tubes comes up against mechanically feasible limits for wall thicknesses of less than 30 µm. Such types of production-limited wall thicknesses, however, run diametrically counter to the requirement for the thinnest possible diameter of the distal end of the catheter.

According to European published patent application EP 1 813 367 A2, markers are alternatively formed by metal injection. For this purpose, the X-ray-opaque metals are dispersed in the melt.

BRIEF SUMMARY OF THE INVENTION

An object of the present invention now lies in providing small dimension markers made of X-ray-opaque material, without having to contend with the disadvantages of small bands. An object of the present invention is thus to provide a method by which markers can be created, which overcome the disadvantages mentioned above, in particular to create a method for the production of markers having wall thicknesses of significantly less than 20 µm.

To achieve this object, the markers are produced by electroplating. With electroplating the markers can be constructed individually. Cutting lengths and the associated deformation, in particular formation of burrs, are thereby eliminated. Electroplating even makes possible the production of non-self-supporting markers or markers with straight edges.

According to the invention, the previously required cutting of the markers is eliminated, so that the mechanical strength required for the cutting is no longer required. For the production of markers according to one embodiment, these can be produced on a substrate having the dimensions of the catheter onto which the completed marker is to be pushed. For this purpose, the substrate is merely removed from the marker after the production of the marker. In this way, several markers can be simultaneously generated with precise final dimensions on a small metal rod or small metal tube provided with resist walls. Compared with cutting from a tube, this individual construction of markers results in no deformation, particularly no formation of burrs. In particular, in the case of the construction of a marker on a substrate, this makes it possible to map edges with precise dimensions. Therefore, according to the invention, markers for polygonal catheters can also be produced.

Alternatively, particularly thin markers, in particular non-self-supporting markers, are generated in boreholes of a substrate. Non-self-supporting markers are then mounted on the catheter before the substrate is finally removed from the marker.

With electroplating markers having a wall thickness of less than 20 µm can be produced, in particular markers with a wall thickness of 5 to 15 µm. Such thin markers have only a very slight build-up. This is particularly advantageous for particularly thin catheters and at least clears the way for the further size reduction of catheters.

Electroplating also makes possible wall thicknesses of up to 100 µm. With electroplating, outer diameters between 30 and 600 µm can be produced.

According to the invention, self-supporting markers having an outer diameter between 40 and 80 µm, in particular between 50 and 70 µm, are provided. The inner diameter of a self-supporting marker having an outer diameter of 40 µm still equals at least up to 20 µm. In the case of self-supporting markers having an outer diameter of 80 µm the inner diameter equals up to 50 µm.

It has proven effective to produce the markers in a length of 0.1 to 5 mm, in particular 0.5 to 2 mm. Proven marker materials are gold and platinum.

For the production of self-supporting markers according to one embodiment, small rods with a copper surface are suitable, around which annular walls made of resist are arranged, in order to define the length of the markers. With the shaft diameter, the inner diameter of the marker is fixed in a particularly simple and very precise way. Since the length of the marker is defined by the spacing of the resist walls running around the shaft, the marker grown on the copper surface does not need to have the mechanical stability that drawn tubules need in order to be able to be cut.

Especially thin-walled markers, in particular non-self-supporting markers, are preferably generated in boreholes of a copper substrate by electroplating of the borehole walls. This method allows a particularly high deposition rate and distinguishes itself by high efficiency.

The method according to the invention for the production of a medical marker made of an X-ray-opaque material is characterized in that the method has the steps:
  a) photolithographic application of a mask on a substrate;
  b) deposition of the X-ray-opaque material of the marker on the substrate;
  c) removal of the mask; and
  d) elimination of the substrate.

The core concept of the invention lies in that the X-ray-opaque material of the medical marker is applied onto a substrate. Here, a mask deposited on the substrate specifies the shape and wall thickness of the marker. No mechanical processing of the marker is needed after removal of the mask and elimination of the substrate. Consequently, no material-fit connection of parts and/or a force-loaded tapering of the marker is necessary. Instead, the deposition of the X-ray-opaque material on the substrate is sufficient. The photolithographically deposited mask here forms a negative shape for the resulting shape of the marker. With the help of the method disclosed according to the invention, markers can be created whose wall thicknesses lie significantly below markers produced with conventional production methods.

The method according to the invention has many advantages. For example, variable geometries of the markers can be achieved, for example polygonal or oval markers. Furthermore, markers produced according to the invention are burr-free. In known production methods, such as cutting lengths of a tube, burrs are always produced. Further, variable wall thicknesses can be produced. Preferably, with the method, markers having outer diameters between 50 and 600 μm and wall thicknesses between 5 and 100 μm, in particular between 5 to 25 μm, can be produced. The described method is preferably used when one has small aspect ratios, such as with non-round markers.

One advantageous variant of the method according to the invention distinguishes itself in that the step a) of the photolithographic application of the mask has the steps:
  i) coating of the substrate with a photoresist;
  ii) exposure of parts of the photoresist forming the mask to light;
  iii) development of the photoresist; and
  iv) removal of non-exposed parts of the photoresist.

The steps claimed according to the invention allow an easy and simple application of the mask on the substrate. Within the scope of the invention, photolithography designates a lithographic reproduction method in which, by exposure to light, a pattern is applied to a substrate. Here, structure information is transferred from a so-called photo-mask to a photoresist. The photo-mask forms the negative for the mask to be formed in the photoresist. The photoresist itself is generally deposited in advance over the entire surface of a substrate. The deposition can be performed here by spin coating, dip coating, or, in the case of solid resists (film resists) by lamination or other methods known to one skilled in the art. After a drying and/or tempering step, the photoresist can be exposed to light and then developed. The exposure of the photoresist is performed with a light source, in particular an ultraviolet (UV) light source. Alternatively, the resist can also be structured with a laser, wherein the resist is removed by the laser. Thus, a transfer of structure information from a negative to the photoresist is possible. After development, the structure information is formed in the photoresist. The non-exposed photoresist is then removed, in particular by etching.

Advantageously, the substrate involves a metal plate, such as a copper plate or a metallized wafer. After the photolithographic structuring of the substrate, a mask is formed whose free spaces are subsequently filled with the X-ray-opaque material of the medical marker. For this purpose, commercially available baths can be used, e.g., fine gold baths with a current density between 1 and 5 $A/dm^2$. Finally, the mask is then removed, which is possible, e.g., using an alkaline bath. After removal of the substrate, the completely produced marker is then obtained.

In addition to the low wall thicknesses that can be produced with the method according to the invention, this method is further distinguished in that nearly any desired shapes and/or structures of the marker can be created. The array of shapes is here limited only by the construction of the mask. Thus, it has proven advantageous if the substrate is constructed with a plate or tube shape. On a plate-like substrate the marker is produced approximately along its longitudinal axis by deposition of the X-ray-opaque material. For tube-like substrates the marker can be produced along its radius by the deposition of the X-ray-opaque material. Tube-like substrates recommend themselves, in particular, when somewhat oval or star-shaped markers are to be produced.

Another advantageous embodiment of the method according to the invention distinguishes itself in that the step b) includes a deposition of the X-ray-opaque material on the substrate and in at least one free space of the mask. The mask deposited by X-ray lithography on the substrate forms the negative for the marker to be created. Here, the photoresist of the mask covers large parts of the substrate. Only at those positions at which the marker is to be created at a later time is the substrate exposed. In particular, it has proven advantageous when the one or more free spaces form a closed path. This closed path or the free space forms each place in which the X-ray-opaque material is deposited. Depending on the deposition method of the X-ray-opaque material, this can be deposited both in the free space of the mask and also on the mask itself. Since the mask is removed after the end of the deposition, any material residues, which lie on the mask, would also be removed. After completion of this step c), the X-ray-opaque material remains on the substrate in the form of the marker. The actual marker is produced only by the removal of the substrate in the scope of step d).

Another advantageous embodiment of the method according to the invention distinguishes itself in that the step a) includes a photolithographic application of a mask on two surfaces, in particular two opposing surfaces of a plate-like substrate. The term "plate-like" here designates a substrate in which two dimensions are significantly larger than a third. By the application of a mask on two surfaces, which advantageously oppose each other and which each have larger dimensions relative to the third, small dimension, the quantity of markers produced with the method according to the invention can in particular be increased.

Another advantageous embodiment of the method according to the invention results from a substrate cut lying under the free space being formed in which the substrate lying under the free space is removed, for the removal in the scope of step iv).

In the scope of this step, not only the non-exposed parts of the photoresist—that is, the free spaces of the mask—are removed, but also the parts of the substrate not covered by the mask. Consequently, an opening is formed in the substrate, wherein this opening essentially corresponds in its shape and profile to the mask lying above. In the scope of the invention, the opening through the substrate is designated as a substrate cut. This substrate cut is any area of the substrate that is similarly eliminated during the removal of the non-exposed parts of the photoresist. Thus, by this step, parts of the substrate are already removed before the actual elimination of the substrate in the scope of step d). Advantageously, in step iv) the substrate lying under the free space is etched away with an acid and/or removed with a laser. In particular, the burning away by a laser makes possible the simultaneous removal of the non-exposed parts of the photoresist and the substrate cuts.

Consequently, in one processing step the free space forming the mask is burned into the photoresist and simultaneously the substrate lying under the free space—the substrate cut—is removed.

The removal of the substrate cut performed in the scope of step iv) is the starting basis for another advantageous embodiment of the method according to the invention. This is characterized in that the step b) of the deposition of the X-ray-opaque material has the following steps:
  aa) passing a flow of an electrolyte through the mask and the substrate cut; and
  bb) depositing the X-ray-opaque material on the substrate from the electrolyte.

In the scope of this embodiment, an electrolyte now flows through the mask and the substrate cut. The electrolyte serves here as a carrier for the X-ray-opaque material, so that it can be deposited on the substrate. Advantageously, the X-ray-opaque material is deposited from the electrolyte onto an inner wall of the substrate cut. Consequently, the deposition of the X-ray-opaque material on the substrate is embodied as a deposition on the inner wall of the substrate cut. The marker thus forms within the substrate.

Depending on the desired form of the marker, parts of the surface of the substrate can still not be covered by the mask. In this case, parts of the marker form both on the inner wall of the substrate cut and also on a surface of the substrate. Alternatively, the mask can completely cover the surface of the substrate and can be interrupted only where the substrate has a substrate cut. In the latter case, the deposition of the X-ray-opaque material of the marker results exclusively within the substrate on the inner walls of the substrate cut.

As an electrolyte, in the scope of the invention, a system is designated which primarily comprises a fluid. The X-ray-opaque material to be deposited is present in ionic form in this fluid, as well as other auxiliary materials for a uniform deposition. In order to enable that uniform deposition, it has proven advantageous if an electrical voltage is applied to the substrate for the deposition of the X-ray-opaque material.

In the scope of the invention, the deposition of the X-ray-opaque material comprises, in particular, a galvanic coating, a chemical coating, as well as an evaporation or sputtering. In the case of galvanic coating, a coating of an electrically conductive material with a metallic layer is performed by reduction of metal ions from a liquid phase on the material surface by electrical current. For the most part, electrolytes are used here that contain aqueous systems with the corresponding metal ions, wetting agents, and other auxiliary aids, such as grain refiners. By dipping of electrodes into this electrolyte, the metal ions can be reduced at the cathode (work piece=negative pole) and in this way the metal layer can be constructed. The galvanic coating is also called electroplating. In the case of external, currentless or chemical coating, no external electrical current is required for the reduction of ions. A targeted addition of reduction agents is here responsible for the deposition.

Furthermore, it is advantageous if in step d) the substrate is dissolved in an acid. Such a type of elimination of the substrate leads to no damage to the marker. The X-ray-opaque material of the marker will comprise, to a large extent, noble metals, such as gold, platinum, tantalum, or niobium. In the corresponding selection of acids, however, these lead to no damage to the named metals.

Another advantageous embodiment of the method according to the invention distinguishes itself in that, after step d), a catheter is guided through the marker. Indeed, the mask is still removed according to the described method, but the catheter to be marked is then guided through the marker before eliminating the substrate. This is particularly advantageous for wall thicknesses of less than 10 μm, since the catheter contributes to a stabilization of the marker. Only after insertion of the catheter into the marker is the substrate then eliminated. At this point, however, the marker already lies on the catheter and is mechanically supported by this.

Another advantageous embodiment of the method according to the invention is distinguished in that at least one free space forms a functional component of the marker. The mask can have a free space, which forms a somewhat circular marker. In addition, further free spaces can still be connected to this free space, wherein these free spaces serve for production of a functional component. As a functional component is to be understood, within the scope of the invention, a component which is not used primarily for marking the catheter. Instead, the functional component can serve to connect the marker more simply and permanently, for example, to the catheter and/or to a stent. Thus, the functional component can be, for example, a clip which is connected to the catheter and/or to a stent with a positive-fit and/or non-positive-fit connection, for example by deformation.

Additional advantages, features, and details of the invention result from the dependent claims and the following description. Here, the features mentioned in the claims and the description can be essential to the invention individually or in any desired combination.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
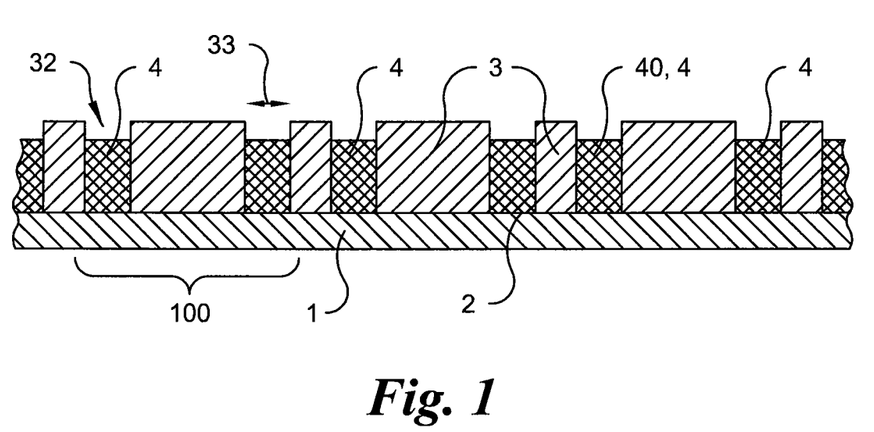
FIG. 1 is a schematic, cross-sectional view of a section of substrate having a photoresist layer coated and developed thereon for forming multiple markers in respective spaces between the photoresist walls, according to one embodiment of the method of the invention.

In one plating method the marker 4 is electroplated on a substrate 1 according to FIG. 1 on the remaining copper surface 2 between the resist walls 3. After the electroplating, the copper substrate 1 and the resist 3 are dissolved, so that the markers 4 generated on this substrate remain.

On a copper surface 2 according to FIG. 1, small aspect ratios, thick wall thicknesses, or non-round markers can be produced with high precision. The marker bodies can have any shape, for example, oval or star-shaped forms. For this purpose, according to FIG. 1 a metal plate 1, for example made of copper or a metallized wafer, is coated on its surface 2 with a photoresist 3. The photoresist 3 is structured photolithographically, and on this photoresist the resulting pits or structures are filled with metal. For this purpose, commercially available baths are used. For example, gold can be deposited from a fine gold bath at current densities around 1 to 5 A/dm$^2$. The resist 3 is removed, for example, with alkaline strippers. The marker 4 is obtained by the removal of the base plate (substrate) 1. Suitable base plates 1 are based on copper or are wafers. The removal of the base plate 1 is performed by etching away this plate or, in the case of a wafer, by removing the metallization.

Figure 2:
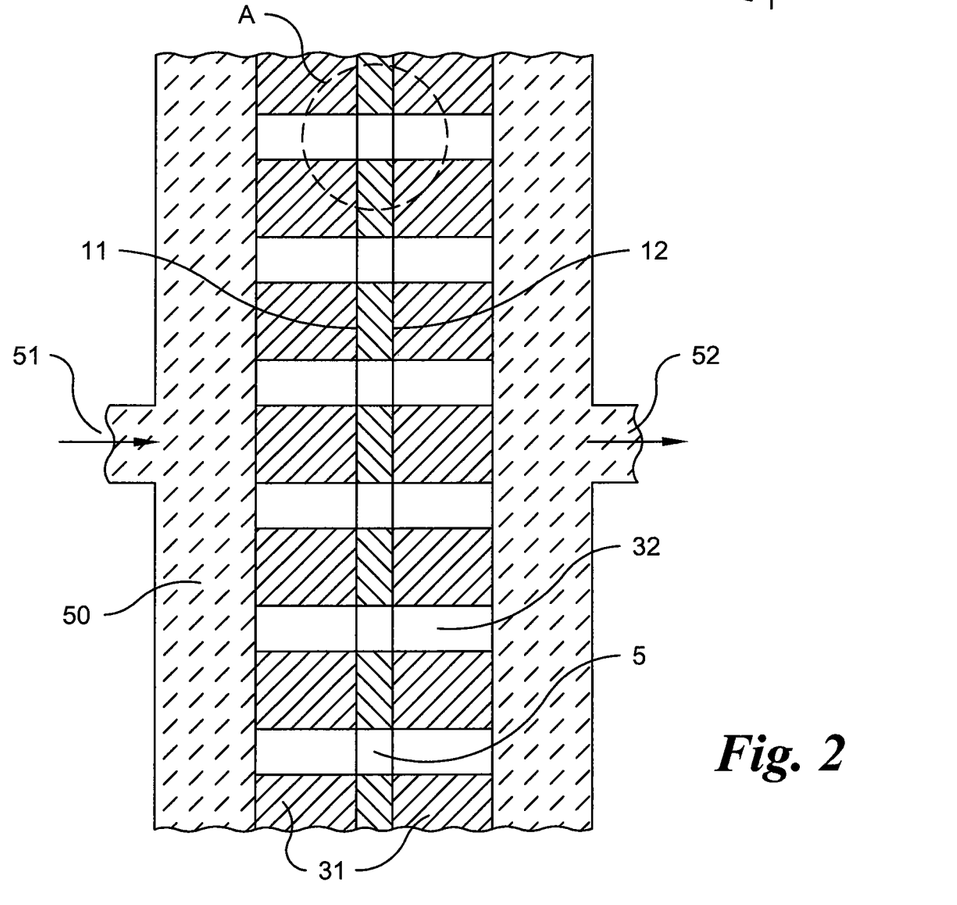
FIG. 2 is a schematic, cross-sectional view of an electrolyte system for plating a copper substrate having boreholes, according to another embodiment of the method of the invention.

For increasing the current densities, according to the method of FIG. 2 it is ensured that the metal ions to be deposited can come to the substrate 1 not just from one side. FIG. 2 is suitable for high aspect ratios and low wall thicknesses. According to FIGS. 2 and 2A, a metal plate 1 is coated on both sides with a photoresist 3 and then structured on both sides. Then the metal plate 1 is etched, so that continuous holes 5 are produced. Then the plate is flushed and brought into the electrolytes 50, in particular gold electrolytes. Then the deposition of the markers 4 into the holes of the plate is performed. Here, the electrolyte 50 could be pumped through the holes 5 and in this way current densities of 5 to 10 A/dm$^2$ can be achieved. One can, indeed, strip the resist and dissolve the plate, but first, in particular, the part to be marked is pushed through the marker 4 and only then is the plate 1 removed. Alternatively, the holes 5 can also be produced in the plate by drilling or erosion, instead of by etching. In this way, star-shaped or oval tubules 4 or rings 4 can be produced.

Figure 3:
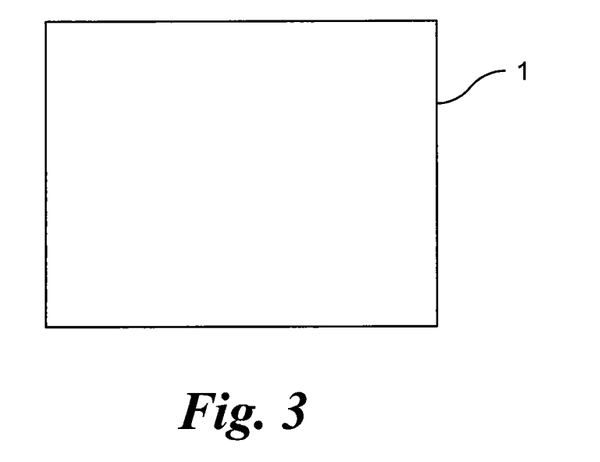
FIG. 3 is a schematic plan view of a substrate according to the embodiment of FIG. 1.
Figure 4:
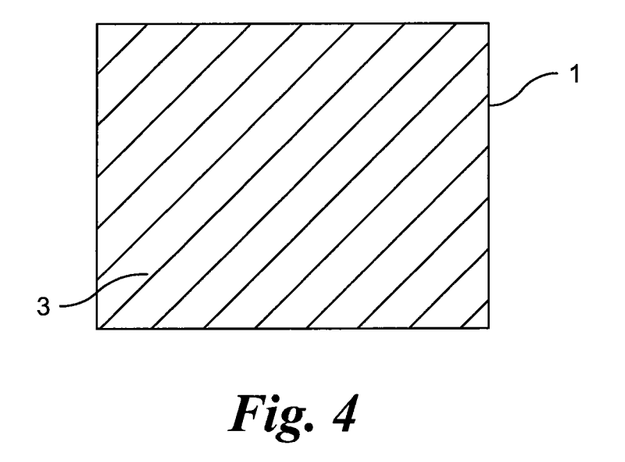
FIG. 4 is a schematic plan view of a deposition of a photoresist on the substrate of FIG. 3.

In FIG. 3, an exemplary embodiment of a substrate 1 is shown. This substrate 1 has a plate-like construction and thus has two dimensions that are large compared with the third dimension that runs into the plane of the drawing. Substrate 1 advantageously involves a metal, such as copper or a metal-coated wafer. The substrate 1 is coated with a photoresist 3. Here, methods can be used which are known to those skilled in the art from the prior art. Each coated substrate, as shown in FIG. 4, is then exposed to light by a photo-mask. In this way, exposed parts 34 and non-exposed parts 35 are produced on the photoresist 3 (see FIG. 5). Then development is performed, in particular chemical development, of the photoresist 3. Then the non-exposed parts 35 of the photoresist 3 can be removed. A substrate 1 then remains on which a photoresist 3 is deposited, such that this has free spaces 32 in which the substrate 1 is not covered by the photoresist 3.

Figure 5:
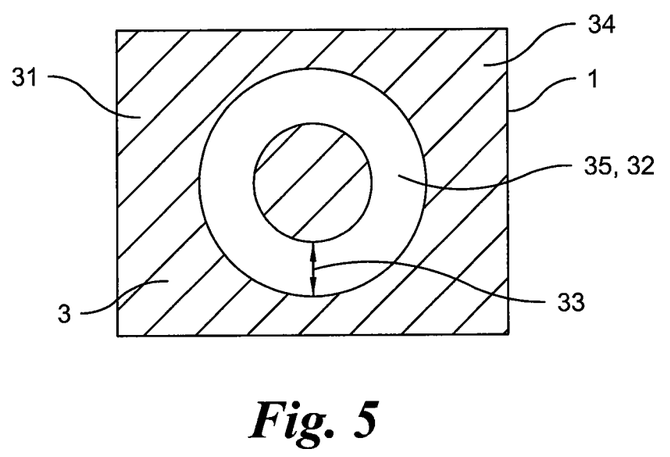
FIG. 5 is a schematic plan view of the substrate and photoresist of FIG. 4 with a formed mask.

FIG. 5 shows that the mask 31 leaves open a ring-shaped free space 32. In this space, the substrate 1 is not covered by the photoresist 3. A width 33 of the free space 32 corresponds to a wall thickness of the marker to be produced.

Figure 6:
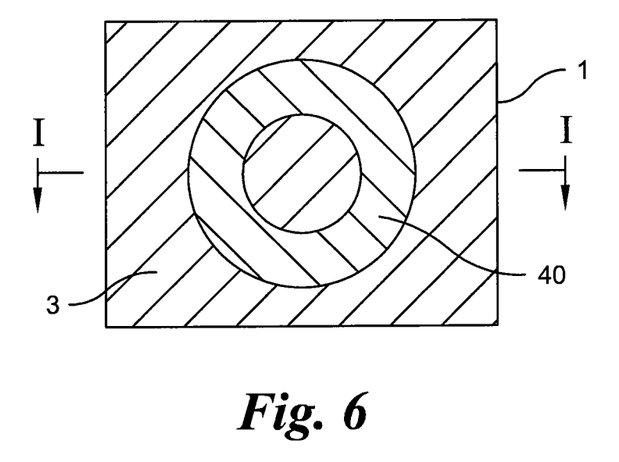
FIG. 6 is a schematic plan view of the substrate with photoresist and formed mask of FIG. 5, after the deposition of an X-ray-opaque material.
Figure 7:
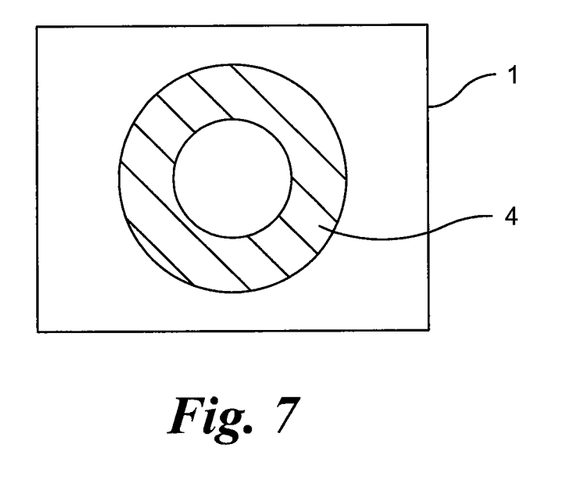
FIG. 7 is a schematic plan view showing removal of the mask.
Figure 8:
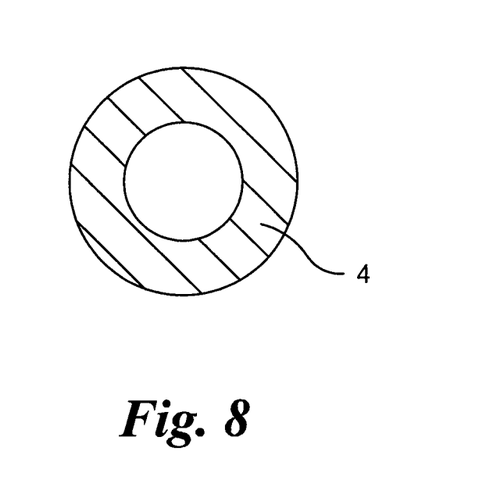
FIG. 8 is a schematic plan view of a marker according to the method of the embodiment of FIG. 1.

After the completion of the photolithographic application of the mask 31 on the substrate 1, the X-ray-opaque material 40 of the marker 4 is deposited on the substrate 1. FIG. 6 shows this step. As is seen, the X-ray-opaque material 40 was inserted into the free space 32 of the mask 31. By the method according to embodiments of the invention, markers 4 can be generated that have wall thicknesses between 5 and 25 μm. The wall thickness of the marker 4 is here dependent on the width 33 of the free space 32, since this is used as a pattern for the later shape of the actual marker 4. After the deposition of the X-ray-opaque material 40 of the marker 4 on the substrate 1, the mask 31 is removed in another step c). FIG. 7 shows this step. In this Fig. the marker 4 is shown still arranged on the substrate 1. By the deposition of the X-ray-opaque material on the substrate 1, a surface-covering, material-fit connection between the marker and the substrate can take place. In order to finally obtain the marker, the substrate 1 is eliminated in the scope of step d). The medical marker 4 produced according to the method of this embodiment of the invention is then produced from an X-ray-opaque material 40 as FIG. 8 shows.

FIG. 1 corresponds to a cross section through a substrate according to the cut line I-I of FIG. 6. FIG. 6 here shows only the portion designated with 100 from the substrate shown in FIG. 1. The mask 31 is constructed on the substrate 1 of FIG. 1, such that a plurality of markers 4 can be produced in parallel. As is to be seen, the X-ray-opaque material 40 is supported directly on the substrate 1. The form and construction of the marker 4 is here dependent on the free spaces 32 of the mask 31 that was deposited from the photoresist in a photolithographic method on the substrate 1. The wall thickness of the marker 4 here corresponds to the width 33 of the free space. In the scope of the invention, the photoresist 3 remaining on the substrate 1 is also designated as resist or resist walls.

Figure 9:
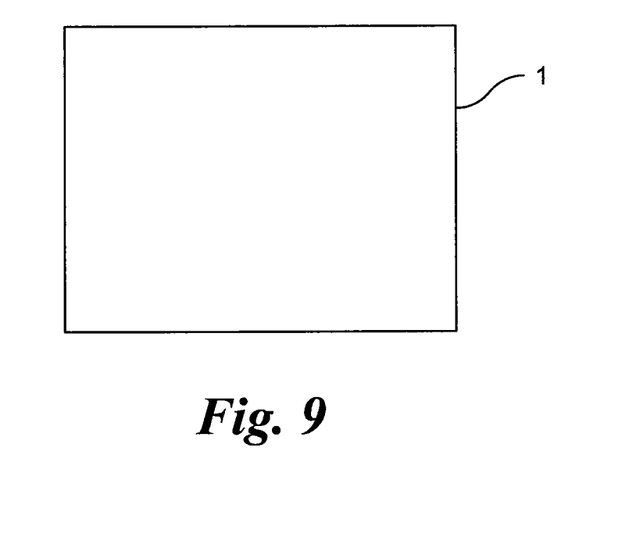
FIG. 9 is a schematic plan view of a substrate for the method of the embodiment of FIG. 2.
Figure 10:
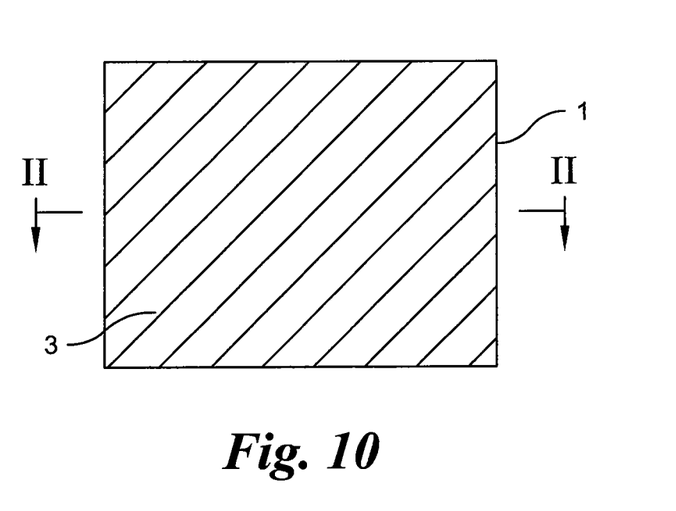
FIG. 10 is a schematic plan view showing coating of the substrate of FIG. 9 with a photoresist.
Figure 11:
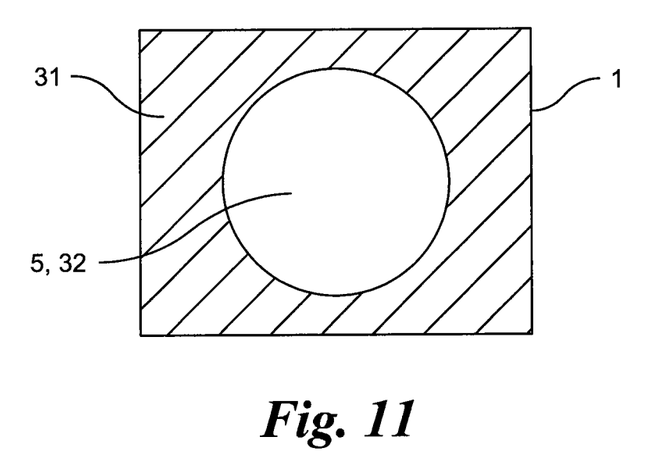
FIG. 11 is a schematic plan view showing a substrate of FIG. 9 having a substrate cut.

Another advantageous embodiment of the method according to the invention is illustrated with reference to FIG. 2, as well as FIGS. 9 to 14. Here, the starting point is a substrate 1, as FIG. 9 shows. Each substrate 1 has a plate-like construction and is coated with a photoresist 3. This step i) takes place on both surfaces 11, 12 of the plate-like substrate 1. FIG. 2 also illustrates this step, which shows a section through the substrate 1 along the section line II-II of FIG. 10. Then the mask 31 is exposed to light and the photoresist 3 is developed (cf. FIG. 10). By the subsequent removal of non-exposed parts of the photoresist 3, the mask 31 is produced (cf. FIG. 11). Deviating from the previously described method, however, in the scope of the removal—step iv—a substrate cut 5 lying under the free space 32 is also formed. In order to form the substrate cut 5, the substrate 1 lying under the free space 32 is removed. Consequently, passages—also designated as holes—are produced in the substrate 1 whose shapes correspond to those of the free spaces 32 of the mask 31. FIG. 11, in particular, should illustrate this step. In the scope of the method according to the invention, not only is structure information formed in the photoresist, which is then seen as the shape of the mask, but this structure information is also formed in the substrate 1. Thus, a kind of sieve plate is formed with an advantageously metallic core—the substrate 1—that is coated on both surfaces 11, 12—the mask 31.

Subsequent to the formation of the substrate cuts 5, it is provided that an electrolyte is used for deposition of the X-ray-opaque material. The electrolyte 50 here flows through the mask 31 and the one or more substrate cuts 5. FIG. 2 illustrates this step, in which it is seen that the substrate 1 with the mask 31 lies in a bath of an electrolyte 50. Here, electrolyte flows 51 from one side into the bath, flows through the mask 31 and, after flowing through the mask 31, flows back out 52 from the bath at an output.

Figure 2A:
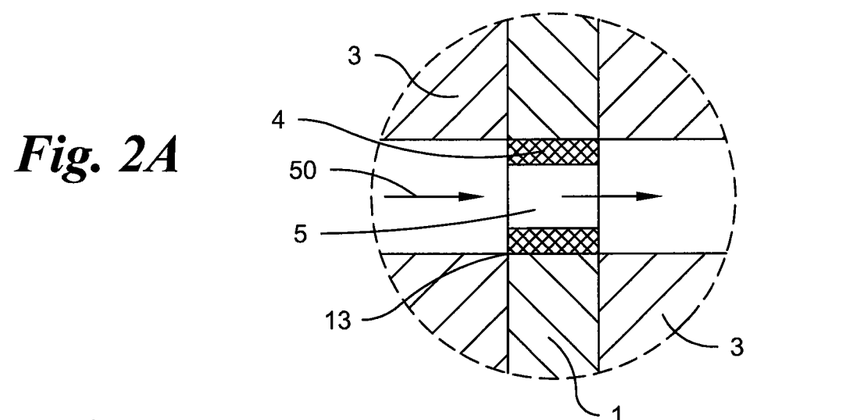
FIG. 2A is an enlarged detail view of the dashed circular portion A of FIG. 2, showing the marker deposited in a borehole.
Figure 12:
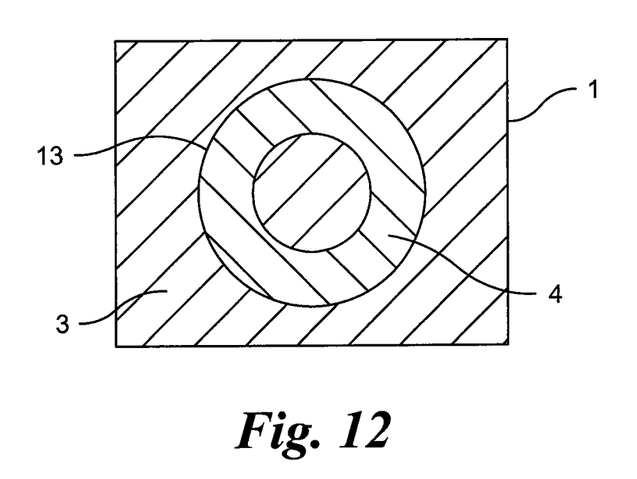
FIG. 12 is a plan view deposition of the X-ray-opaque material on the substrate of FIG. 9.
Figure 13:
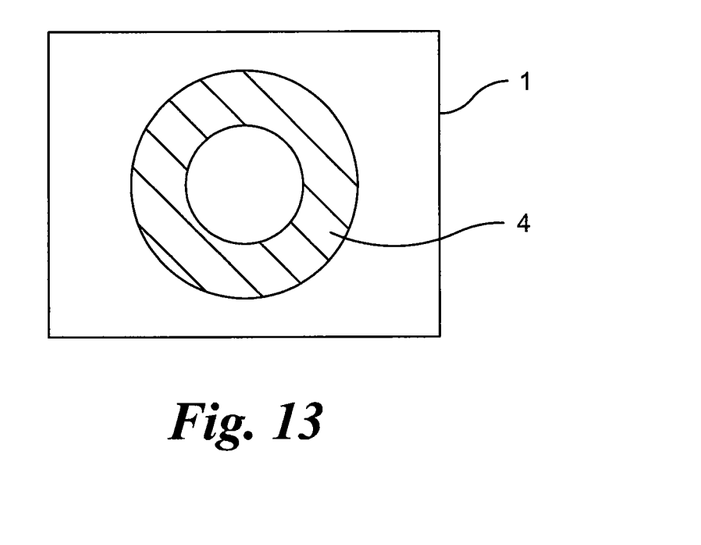
FIG. 13 is a schematic plan showing removal of the mask.
Figure 14:
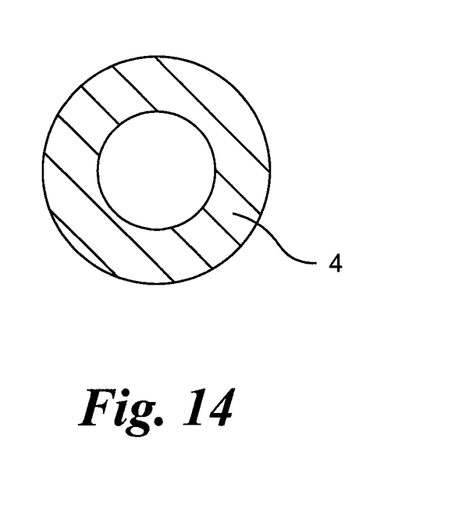
FIG. 14 is a schematic plan view of a marker produced with the method according to the embodiment FIG. 2.

To realize a medical marker 4, it is provided according to the invention that the X-ray-opaque material 40 is deposited on the substrate 1 from the electrolyte 50. The cutout enlargement shown in FIG. 2A shows this step. The electrolyte here flows according to the movement arrow 51 into the mask. In general, there is absolutely no deposition of the X-ray-opaque material 40 on the mask 31 or the photoresist 3. To guarantee this, it has proven advantageous if the photoresist 3 is electrically insulating. To realize a deposition of the X-ray-opaque material, the preferably metallic substrate 1 is provided with an electrical voltage. The resulting electrical current ensures that the metal ions of the electrolyte are reduced to metal on the inner wall 13 of the substrate cut 5. The marker 4 is consequently produced on the passages/holes 5 formed in the substrate 1 through galvanic deposition of the X-ray-opaque material 40 from the electrolyte. FIG. 12 should also clarify this step. It shows a view onto the substrate 1 with the marker 4 accumulated on the substrate 1. The viewing direction here corresponds to the movement arrow 51 from FIG. 2. After completion of the accumulation, the mask 31 is removed, which FIG. 13 should clarify. To then realize the actual marker 4, only the elimination of the substrate 1 is still required, as FIG. 14 illustrates.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for production of a ring-shaped and non-self-supporting medical marker having a wall thicknesses of less than 20 μm and comprising an X-ray-opaque material, wherein the method comprises the following steps:

a) applying a mask with ring patterns formed in registration on two surfaces of a conductive plate-shaped substrate by photolithography;
b) depositing the X-ray-opaque material of the marker in a borehole in the substrate;
c) removing the mask; and
d) eliminating the substrate such that the marker is non-self-supporting,
wherein step a) comprises: i) coating the substrate with a photoresist; ii) exposing parts of the photoresist to light to form the mask; iii) developing the photoresist; and iv) removing non-exposed parts of the photoresist by forming the borehole through the substrate and at least one ring-shaped free space of the mask, such that the substrate lying under the at least one ring-shaped free space is removed, and
wherein step b) comprises: aa) passing a flow of electrolyte through the mask and the borehole; and bb) depositing the X-ray-opaque material from the electrolyte onto a wall of the borehole by galvanic deposition.

2. The method according to claim 1, wherein step b) includes depositing the X-ray-opaque material on the wall of the borehole and in the at least one free space of the mask.

3. The method according to claim 2, wherein the at least one free space forms a functional component of the marker.

4. The method according to claim 1, wherein in step a) iv) the substrate lying under the at least one free space is etched away with an acid and/or is removed with a laser to form the borehole.

5. The method according to claim 1, wherein in step d), the remaining portions of the substrate are dissolved in an acid.

6. The method according to claim 1, wherein after step c) and before step d), a catheter is guided through the marker.

* * * * *